United States Patent [19]

Blake, III et al.

[11] 4,408,603

[45] Oct. 11, 1983

[54] SURGICAL DEVICE

[76] Inventors: Joseph W. Blake, III, RR #2, Box 106, Kitchewan Rd., South Salem; Jack W. Kaufman, 357 Frankel Boulevard, Merrick, both of N.Y.

[21] Appl. No.: 391,367

[22] Filed: Jun. 23, 1982

Related U.S. Application Data

[63] Continuation of Ser. No. 200,407, Oct. 24, 1980, Pat. No. 4,372,316, which is a continuation of Ser. No. 63,268, Aug. 2, 1979, Pat. No. 4,296,751.

[51] Int. Cl.$^3$ ............................................. A61B 17/12
[52] U.S. Cl. ................................. 128/325; 29/243.56; 227/DIG. 1; 206/339
[58] Field of Search ................... 128/325, 326, 334 R, 128/335, 336, 337; 72/410; 29/243.56; 206/339, 340

[56] References Cited

U.S. PATENT DOCUMENTS

| 2,744,251 | 5/1956 | Vollmer | 227/DIG. 1 X |
| 3,047,874 | 8/1962 | Kelsey | 72/410 |
| 3,098,232 | 7/1963 | Brown | 128/334 R |
| 3,230,758 | 1/1966 | Klingler | 72/410 |
| 3,646,801 | 3/1972 | Caroli | 128/334 R X |
| 3,844,289 | 10/1974 | Noiles | 128/334 R |
| 4,166,466 | 9/1979 | Jarvik | 227/19 X |

Primary Examiner—Michael H. Thaler
Attorney, Agent, or Firm—Charles J. Knuth; Peter C. Richardson; Harold W. Ordway

[57] ABSTRACT

A surgical clip applicator includes a forceps and a detachable cartridge containing a string of clips which are fed seriatim between the anvils of the forceps jaws.

2 Claims, 13 Drawing Figures

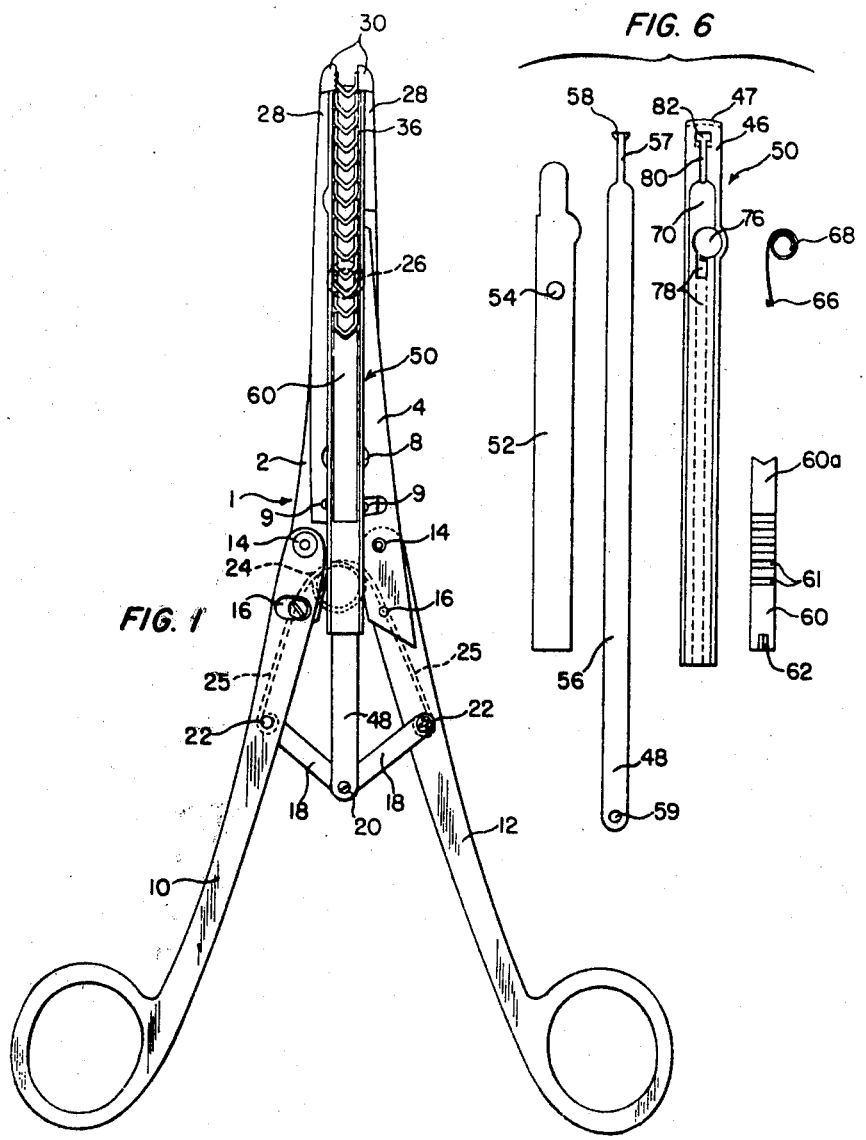

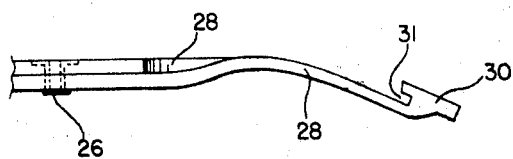
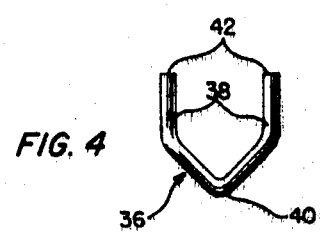
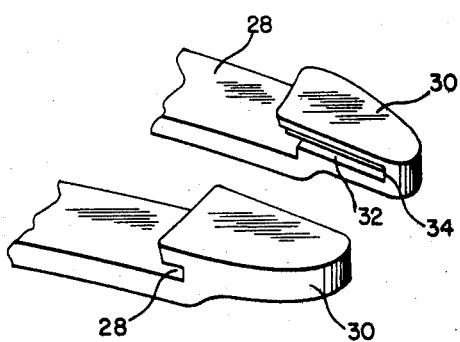
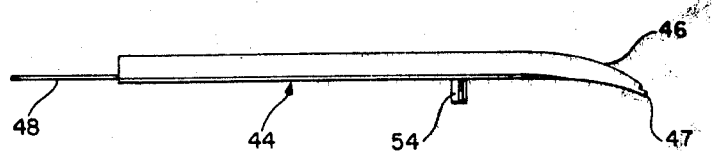

SURGICAL DEVICE

This is a continuation, of application Ser. No. 200,407, filed Oct. 24, 1980 now U.S. Pat. No. 4,372,316 which in turn is a continuation of application Ser. No. 063,268, filed Aug. 2, 1979, now U.S. Pat. No. 4,296,751.

BACKGROUND OF THE INVENTION

1. Field of the Invention

This invention relates to surgical devices in general.

More particularly, the invention relates to a magazine-loaded suturing device of the type using suturing clips, and to a magazine for use with such a device.

Still more specifically, this invention relates to a suturing device and a magazine of the type under discussion, wherein the suturing clips are automatically advanced to their position of use.

2. The Prior Art

Certain types of suturing are still, and probably always will be, performed by hand. Other types of suturing, however, such as skin sutures and hemostatic sutures, are performed with the aid of staple-like metal clips which are driven into the skin or, in the case of hemostatic clips, tightly squeezed about a blood vessel to stop the flow of blood through the same.

The invention will hereafter be described for purposes of explanation with reference to hemostatic applications. It should be understood, however, that it has more general applicability in the field of surgical suturing. It should also be understood that the term "suturing" as used herein is intended to carry the broadest meaning, i.e. to embrace hemostatic, skin, as well as other types of suturing in which suturing clips are employed.

In the prior art it is known to employ e.g. hemostatic forceps which are individually loaded with clips. In practice this means that at least two forceps may be used during the suturing operation: while the surgeon applies a hemostatic clip to a bloodvessel with one forceps, an assistant (nurse) standing behind him inserts a single clip between the jaws of the second forceps, ready for use. The surgeon hands the used forceps back over his shoulder to be reloaded and the assistant hands him the newly loaded forceps in exchange. This exchange continues until suturing is completed. It is self-evident that this procedure is not very efficient, it ties up the assistant who could be performing some other function, and (particularly important in an emergency) it slows the surgeon down.

A proposal has been made to provide a magazine-loaded hemostatic forceps with semi-automatic clip feed. This has not found acceptance because the surgeon is required to perform a "cocking" operation after each clip is set; it is this operation which advances the next clip to operative position. Aside from the obvious disadvantage inherent in the lack of a fully automatic feed, the cocking motion is cumbersome and puts a strain on the surgeon's hands, which is definitely undesirable in terms of his steadiness and accuracy.

Solutions proposed in the stapler art, for devices used in closing boxes and the like, have been found not to be workable in the medical field. Suturing equipment is precision surgical equipment which must be small (there is the problem of access to certain wound areas), light (so as not to tire the surgeon and to permit ready manipulation) and sterilizable. The known staple solutions cannot be successfully integrated in equipment having to meet these requirements. A drastic departure from the prior art solutions is therefore required to arrive at the desired goal.

SUMMARY OF THE INVENTION

Accordingly, it is an object of the present invention to overcome the disadvantages of the prior art.

More particularly, it is an object of the invention to provide an improved suturing device which is not possessed of the prior art disadvantages.

Still more specifically, it is an object of this invention to provide a cartridge-loaded suturing device, and a cartridge or magazine for use with such a device, which improve upon the prior art and avoid the drawbacks thereof.

A concomitant object is to provide such a device and a cartridge or magazine for use therewith, which use surgical clips for suturing.

Yet a further object is to provide a device and cartridge of the type mentioned above, which are relatively small and of light weight.

Still another object is to provide such a device and cartridge which are inexpensive to produce.

Yet another object is to provide such a device and cartridge which can be produced simply and inexpensively enough for "one-way" use, i.e. to be discarded jointly or severally when the surgical clips in the cartridge are used up.

In keeping with these objects, and with still others which will become apparent hereafter, one aspect of the invention resides in a surgical device, particularly a hemostatic device. Briefly stated, such a device may comprise a forceps having a pair of cooperating jaws movable between an open and a closed position. The forceps may be made as metal stampings to reduce their manufacturing cost since primarily only the jaws will require precision tolerances. However, it is also conceivable to make them of synthetic plastic materials, or to make them in part of metal (e.g. the jaws) and in part of synthetic plastic material.

The device further comprises means for feeding surgical suturing clips (such as blood-vessel occluding clips) to the jaws of the forceps. Such means may comprise a cartridge or magazine adapted to accomodate a string of the clips (the term "string" embraces the possibility of having the clips unconnected to each other and arranged in a row in the cartridge, but may also embrace a row of connected clips). Means are provided for advancing the string of clips in the magazine towards the jaws of the forceps, so that the respectively leading clips are inserted seriatim between the jaws while the same are in their open position, so as to become squeezed between the jaws when the same move to their closed position. In addition, means are provided for retracting all but the respectively leading clip of the string in direction away from the jaws prior to movement of the jaws towards their closed position.

The jaws of the forceps are curved to one side of the general plane of the forceps so as to provide "presentation", i.e. to enable the surgeon to more readily observe his suturing operation. The cartridge is elongated and located in a plane parallel, or substantially parallel, to the general plane of the forceps and in which each of the clips is located in its entirety.

The novel features which are considered as characteristic for the invention are set forth in the appended claims. Both the construction and method of operation of the invention as well as additional objects and advantages thereof, will however be best understood from the following description of specific embodiments in connection with the accompanying drawings.

BRIEF DESCRIPTION OF THE DRAWING

FIG. 1 is a plan view showing one side of a forceps;

FIG. 2 is a side view, showing only the jaw area of the forceps in FIG. 1;

FIG. 3 is a fragmentary close-up view of the jaws in FIG. 2, partly sectioned;

FIG. 4 is a plan view of a surgical clip to be used with the forceps of FIGS. 1-3;

FIG. 5 is a somewhat diagrammatic side view of a cartridge according to the invention, shown in assembled condition;

FIG. 6 is a plan view of the underside, showing the cartridge elements in disassembled condition;

DESCRIPTION OF PREFERRED EMBODIMENTS

Figure 7:
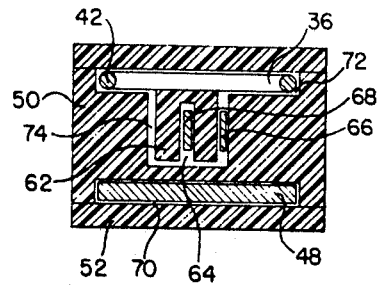
FIG. 7 is a section on line VII—VII of FIG. 8.

An applicator for applying the cartridge-supplied clips is illustrated in FIGS. 1-3 in form of a hemostat forceps, by way of explanation. Reference numeral 1 identifies the forceps in toto. In the usual manner the forceps 1 has two arms 2, 4 which are pivotally connected by means of a pivot 26 on one and a transverse slot 8 in the other arm. The arm 4 is also provided with a pair of transversely spaced cartridge retaining and stabilizing stops 9 and with a hole 26 which receives a pivot (to be discussed infra) of the cartridge.

Arms 2, 4 have respective handles 10, 12 which, in this particular embodiment, are separate elements pivoted to the arms 2, 4 at pivots 14, 14. In addition, each handle 10, 12 is connected to the associated arm via a slot-and-pin connection 16 (one shown in detail in FIG. 1; the other is located at the other side of the forceps). The connections 6, 8 and 16 provide for a lost-motion movement when the arms 2, 4 are pivoted relative to one another in a sense causing the end section 30 of their curved (see FIG. 2) jaws 28 to approach one another. The significance of this lost-motion movement will become apparent as the description proceeds.

Handles 10, 12 are connected by a link 18 having its two bars pivoted to each other at 20 and to opposite sides of arms 10, 12 at 22, 22. A torsion spring 24 has two legs 25 connected to the pivots 22, 22 and thus permanently tends to urge the arms 2, 4 apart to the position illustrated in FIG. 1. Arms 10 and 12 are also urged to the open position.

FIG. 2 shows that the jaws 28 and their end sections 30 are curved to one side of the general plane of the forceps 1, in order to provide "presentation", i.e. to assure that the view of the wound area being worked upon by the surgeon is not obscured by any other part of the forceps. In FIG. 3 the end sections 30 will be seen to be provided in their facing surfaces with longitudinal grooves 32 for the surgical clips. These grooves are closed at their front ends, to provide end stops (abutments) 34 for the clips to be supplied by the magazine.

A single clip 36 is illustrated in FIG. 4 and will be seen to be of generally U-shaped outline in plan view, having two arms 38 which are connected by a bight 40 and have free ends 42 adapted to abut against the end stops 34.

It should be understood that the illustration in FIG. 4 is by way of example only, and that a clip suitable for use in the cartridge of the invention may depart in various ways from the shape shown in FIG. 4 and still be suitable.

Details of an exemplary cartridge, for use with the applicator of FIGS. 1-3, will now be described with reference to FIGS. 4-11.

FIG. 5 is a somewhat diagrammatic side view, showing the cartridge 44 in assembled condition and illustrating its curved front end portion 46 (the curve is complementary to that of the forceps jaw 28) and a portion 48 of a clip retractor which extends out from the back end of the cartridge. A pivot 54 is to be inserted into the hole 26 of the forceps 1.

The individual elements of the cartridge 44 are shown in FIG. 6, which illustrates the cartridge in a plan view and in disassembled form. The main cartridge body is identified with reference numeral 50, and in the assembled condition, will be covered by the illustrated backing plate 52 on which the previously mentioned pivot 54 is provided (of one piece with it or suitably secured to it). The clip retractor is identified with reference numeral 56; it is a length of e.g. spring steel whose purpose will become clear in due course. The front portion 57 of the retractor 56 is of reduced width and carries at its free end a head 58 of e.g. generally triangular shape. The rear portion 48 (see FIG. 5) is provided with means 59 (e.g. a hole, a projection or the like) for connecting it to the center pivot 20 of link 18.

The cartridge body 50 will accommodate a string of clips 36 in unconnected form; i.e. they will be sequentially but individually located in a clip track of the body 50, to be fed forwardly (to the front end 46) by spring action. For this purpose a clip follower 60 is provided, in form of a strip-shaped element which is provided in its front end with a notch shaped to accomodate the bight of the last clip 36 in the string. The rear (trailing) end of follower 60 has a tail piece 62 projecting to one major side of the follower (compare FIG. 7) and provided with a slot 64 in which a hook-shaped end portion 66 of the clip-biasing spring 68 is engageable. At least the center portion of follower 60 is provided with transversely extending ridges and grooves 61, so as to make the follower more flexible and enable it to follow the curvature of the front end 46 of the cartridge.

The spring 68 is a constant-force coil spring (commercially available under the tradename "Neg-A-Tor") which exerts constant forward spring force upon the follower 60 (and via the same upon the string of clips 36) regardless of the degree of extension of the spring. In other words: the tension exerted upon the clips 36 when a full string is present in the cartridge and the spring is extended to its maximum, is the same as the tension exerted upon the last remaining clip in the cartridge after all other clips in the string have already been depressed and used.

That side of body 50 which will face towards the forceps 1 when the cartridge 44 is installed on the same, is formed with a recessed track 70 in which the clip retractor 56 slides; in the assembled condition of the cartridge this track 70 is covered by plate 52. Towards the front end of the cartridge the track 70 merges into a slot 80 slightly wider than the portion 57 of the retractor; this slot 80 extends through the cartridge body 50 and opens into a clip track 72 (FIG. 7) which is formed in the other side of body 50, i.e. the side which faces away from the forceps 1.

A cavity 76 is formed in that side of body 50 which has the retractor track 70 and has an open end flush with the bottom surface of track 70 (FIG. 9); i.e. the cavity 76 is recessed below the level of track 70. Also formed in the body 50, offset to one side (FIG. 7) are a track and an opening 78 in which the extended portion of spring 68 and the tail 62 of the follower 60 move. The follower itself moves in the clip track 72 behind the string of clips and its tail extends into the track 78 which is open to the clip track 72.

Near its front end the body 50 is provided, at the front of slot 80 and in the bottom surface of the clip track 72, with a recess 82 dimensioned to accomodate the head 58 of retractor 56, so that the head, when located in the recess 82, will be flush with (or recessed below) the aforementioned bottom surface and not interfere with the forward movement of the clips 36 which move right over and past it. Inclined ramps or camming surfaces 81 (FIG. 11B) are located at either side of slot 80 and rise out of the recess to the level of the bottom surface of the clip track 72.

Figure 10:
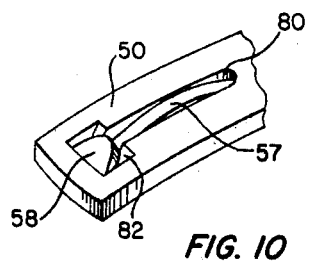
FIG. 10 is a fragmentary perspective view, showing a detail of the front end of the cartridge.
Figure 9:
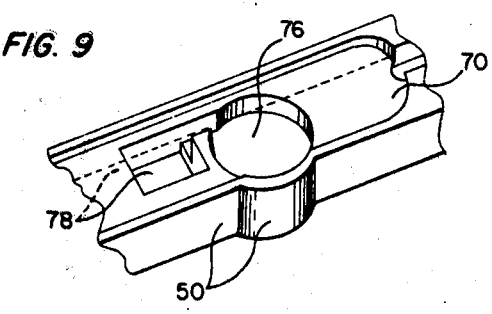
FIG. 9 is a fragmentary perspective view with parts omitted for clarity.
Figure 8:
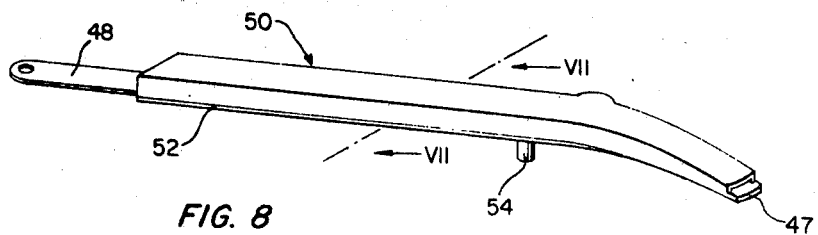
FIG. 8 is a diagrammatic perspective view of the assembled cartridge.
Figure 11A:
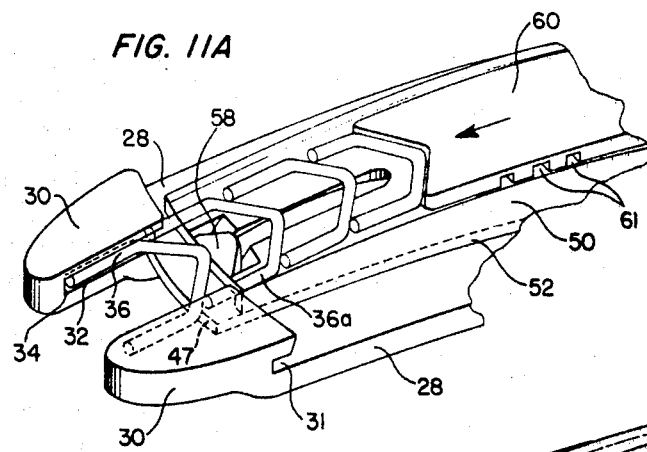
FIGS. 11A–11C are simplified action diagrams showing the operation of the cartridge.
Figure 11B:
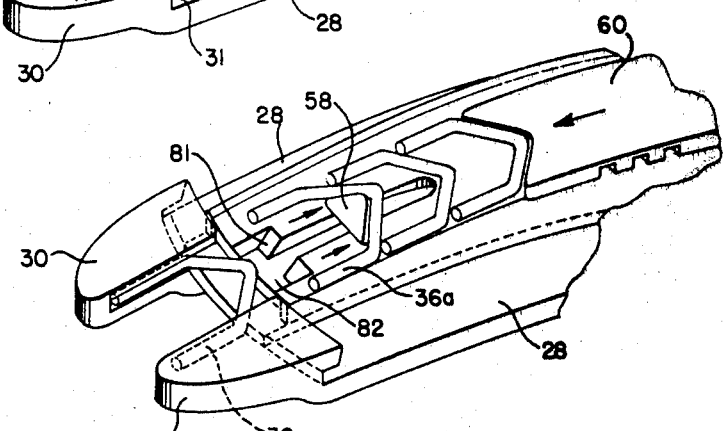
Figure 11C:
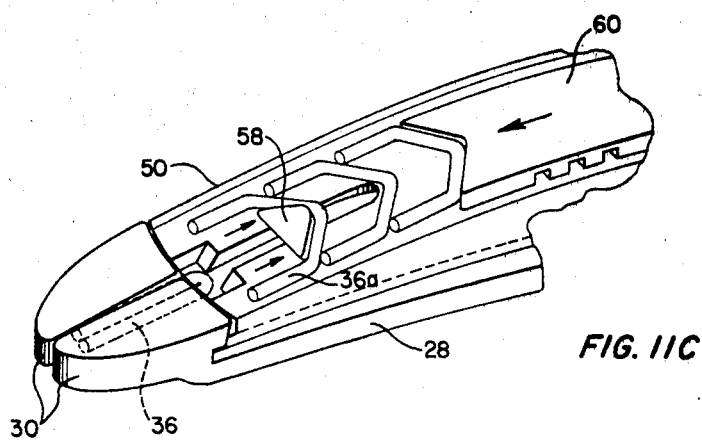

The portion 46 of the cartridge 44, or rather of the body 50 in particular, is curved as illustrated in FIG. 5. This curvature follows that of the forceps jaws 28 and its purpose is to allow the portion 46 to snugly fit against the jaws 28. Correspondingly, the retractor track 70 and the clip track 72 are also curved. The front portion 57 of the retractor 56, however, is curved more strongly than the front portion of the tracks 70, 72. The portion 57 of retractor 56 extends through the slot 80 from the track 70 into the track 72 (i.e. from one side of the body 50 to the other as shown in FIG. 10). The springback tendency of the portion 57 (the retractor is of spring steel or the like) is counter to this deflection from track 70 into track 72. Consequently, the head 58 is always biased into contact with the bottom surface of track 72. Therefore the head 58 snaps into the recess 82 when the retractor is far enough forward to permit this, i.e. when head 58 is in registry with the recess. In this position the head is located beneath the path of the clips advancing in track 72, so as not to interfere with them. When the retractor is moved backwards, however, the head 58 slides up on the ramps 81 and enters into track 72; i.e. it becomes located in the path of the clips 36. More specifically, the head then enters into the space between the legs 38 of the upstream clip 36a which is located immediately behind the leading clip (FIG. 11A), and upon further retraction of retractor 56 the head 58 engages the inside of the bight 40 of this upstream clip 36a and retracts the same (and thereby all other clips behind it) away from the front end of the cartridge. The purpose is to move clip 36a out from between the closing jaws 28, 30 (FIG. 11B) so that these can cinch the leading clip 36 between them (e.g. about a blood vessel to occlude the same) as shown in FIG. 11C. When the jaws re-open the retractor 56 slides forwardly, head 58 snaps back into recess 82 and the next clip (i.e. 36a) can now enter between the portions (anvils) 30 of jaws 28.

The operation of the device will be understood from what has been discussed thus far:

The cartridge 44 is mounted to the forceps 1 by placing its portion 47 into the notches 31 of anvils 30, inserting pivot 54 into hole 26 and connecting means 59 to the center pivot 20 of link 18. When the handles 10,12 are now squeezed towards one another the two parts of link 18 pivot about the center pivot 20 and the end pivots 22; since center pivot 20 is located rearwardly of a line connecting the end pivots 22, the approach of the end pivots 22 towards one another has the effect of shifting the center pivot 20 still further rearwards of this line. The retractor 56 is connected to the center pivot and such rearward shifting therefore causes it to slide backwardly, so that head 58 moves from the position of FIG. 11A to that of FIG. 11C. Since the cartridge has just been newly installed, no clip will at this time be located between anvils 30 so that only a retraction of the string of clips takes place in the cartridge.

As soon as the pressure on the handles 10,12 is released, they are forced apart (to the FIG. 1 position) by the spring 24. In so doing the pivot 20 moves forwardly and allows the spring 68 to assist in sliding retractor 56 to forward position (by exerting pressure on head 58 via the string of clips bearing upon it). When head 58 reaches recess 82 it snaps into the same, thereby releasing the leading clip 36 which it has previously held, for advancement into the grooves 32 of anvils 30, until the free ends 42 of its legs 38 come to rest against the end stops 34. During this movement the next-following clip (e.g. clip 36a) has advanced with parts of its own legs between the anvils 30 and would prevent proper operation of the device, if allowed to remain in place. In order, however, to affix the leading clip 36 (e.g. about a blood vessel), the user must again squeeze handles 10, 12 together so as to crush (crimp) the clip between the anvils 30. In doing so he automatically effects a retracting of all clips (36a, etc.) located behind leading clip 36 (FIG. 11B), so that the device can operate as intended (FIG. 11C). Each successive squeezing of the handles 10, 12 will apply another clip to the wound with the next-following clip moving into readiness between the anvils 30 as pressure on the handles is relaxed between squeezes. This continues until cartridge 44 is empty.

If, after the last clip is used, the now empty anvils 30 were allowed to press directly upon e.g. a blood vessel, they would do severe damage to the same. The invention avoids the possibility by making the follower 60 so long that its front end portion 60a enters into the grooves 32 of anvil 30 after the last clip is used. In other words: as the spring 68 returns to its rest position after the last clip is applied, it urges the front end portion 60a into the grooves 32. This prevents the anvils 30 from being closed directly (i.e. without interposition of a clip) about the bloodvessel and, at the same time, tells the surgeon (who can no longer squeeze the handles together) that the cartridge is empty.

The cartridge 44 is held to the forceps 1 at undercuts 31 and at the pivot 20. It therefore can shift relative to the forceps to a limited extent, in a plane parallel to the general plane of the forceps. The degree of such movement is limited by the abutments 9 between which the cartridge is located. The front end 47 can self-adjust relative to the anvils 30 during use of the forceps, as the comparison of FIGS. 11A–11C indicates.

The purpose of the lost motion afforded by the manner in which handles 10, 12 are mounted on arms 2,4 is to cause (during initial squeezing of the handles 10, 12) the retraction of the retractor 56 and thus of the clips 36, before the jaws 28 and their anvils 30 begin to move towards one another. This allows clip 36a to move out of the way of anvils 30.

It will be appreciated that in the region of the spring cavity 76 the clip track 72 will be separated from the cavity 76 by a thin wall which avoids interference between the clips and the spring. The retractor also aids in centering the clips relative to the anvils by engaging the apex of the bight of the respective clip during retraction and holding it—thereby centering the clip—until the clip is ready to advance between the anvils.

It will also be appreciated that the disclosed embodiment is susceptible to various modifications without departing from the concept of the invention. For example, the handles 10, 12 could be made of one piece with (or at least rigidly connected to) the arms 2, 4. The last motion would then be provided by using (e.g. at the location of hole 26) a transverse slot-and-pin connection for the arms 2,4. The pin itself could be hollow and its hollow interior serve as a replacement for the hole 26. A retainer could be provided for preventing the clip located in the grooves of the anvils from sliding back into the cartridge when the upstream clips are retracted and in the event the surgeon then holds the forceps with the jaws in elevated position.

The spring 24 and links 18 could be replaced by a one-piece unit, e.g. a generally chevron-shaped spring having its ends rigidly connected to the arms 10, 12 and yielding elastically in essentially the same sense as the links 18, so that its center (corresponding to pivot 20) would recede from and approach the jaws 28 in essentially the same manner as the pivot does. The cartridge may also be provided with a releasable retainer for holding the first (lead) clip against being expelled from the cartridge under the pressure of spring 68 until the cartridge is installed in the forceps.

The cartridge and/or forceps may be made wholly or in part of synthetic plastic material. Suitable plastic materials, especially for the cartridge, are polysulfone which is a high-strength autoclavable plastic approved by the Food and Drug Administration for medical use; polycarbonates (e.g. "Lexan"/TM) or acetal (e.g. "Delrin"/TM) which have lesser qualities but are also considerably less costly than the preceding materials. Such plastics may, of course, be reinforced by e.g. carbon fibers or the like.

The cartridge will be disposable, and the forceps may be permanent. The parts of the latter may be stamped from sheet metal (e.g. brass, stainless steel) to reduce manufacturing costs. However, the forceps could itself be disposable together with the cartridge, if it can be made inexpensively enough. For example, the main parts of the forceps except for the arms 2, 4 might be made of synthetic plastic, or even the arms themselves might be made thereof and perhaps only the anvils made of metal. This is primarily a question of using a plastic having sufficient strength to withstand the forces acting upon it during the application (crimping or cinching) of the clips. Arms 2 and 4 may be made of synthetic plastic material and have metal reinforcements.

As mentioned before, the invention—i.e. the cartridge and/or the forceps—is of particular advantage for use in ligating blood vessels. However, the invention is also suitable for use in general suturing and surgical stapling. The shape (outline) of the clips may be varied as required and the free ends of the clips may be pointed for special non-ligating applications. The connection of the retractor 48 to the pivot 20 may be by way of a hole in the retractor (or the link and a pin on the link of the retractor). However, it goes without saying that other connections may be used, such as a snap-type coupling, a wedging coupling, or the like.

While the invention has been illustrated and described as embodied in a hemostat forceps, it is not intended to be limited to the details shown, since modifications and structural changes may be made without departing from the spirit of the invention.

What is claimed as new and desired to be protected by Letters Patent is set forth in the appended claims:

1. A surgical device, particularly a hemostat, comprising
   an applicator having a pair of cooperating jaws provided with anvils and being movable between an open and a closed position; and
   supply means for feeding surgical clips to said jaws, said supply means comprising a cartridge including a housing, a string of clips in said cartridge, means for advancing the string relative to the housing and towards the jaws for seriatim insertion of the respectively leading clip of the string between said anvils while said jaws are in said open position so as to become cinched between said anvils when the jaws move to said closed position, and means for retracting all except the respectively leading clip in direction away from said anvils relative to the housing and prior to movement of said jaws from said open towards said closed position, said retracting means comprising a retracting member mounted for movement between said leading clip and its adjacent clip for urging said adjacent clip and the successive clips away from said anvils;
   wherein each of said clips is generally U-shaped with a pair of free ends interconnected by a bight, said clips being positioned in said housing with the free ends of one clip disposed at the bight of its adjacent successive clip, and said retracting member being mounted for insertion between said bight of said leading clip and said bight of said adjacent clip, whereby movement of said retracting member away from said anvils causes said adjacent clip and said successive clips to move away from said anvils.

2. A cartridge for use with a surgical device, particularly for use with hemostatic forceps, comprising
   a housing having a track provided with an outlet;
   means for advancing a string of surgical clips in direction towards said outlet so that the respectively leading clips of the string are sequentially discharged from the outlet to become cinched by jaws of the surgical device; and
   means for retracting the clips located upstream of the respective leading clip counter to said direction and away from said outlet prior to cinching of the discharged leading clip, so as to avoid interference by the upstream clips with such cinching, said retracting means comprising a retracting member mounted for movement between said leading clip and its adjacent clip for urging said adjacent clip and the successive clips away from said anvils;
   wherein each of said clips is generally U-shaped with a pair of free ends interconnected by a bight, said clips being positioned in said housing with the free ends of one clip disposed at the bight of its adjacent successive clip, and said retracting member being mounted for insertion between said bight of said leading clip and said bight of said adjacent clip, whereby movement of said retracting member away from said anvils causes said adjacent clip and said successive clips to move away from said anvils.

* * * * *